United States Patent
Paik et al.

(10) Patent No.: US 10,555,885 B2
(45) Date of Patent: Feb. 11, 2020

(54) LOW VISCOUS COSMETIC COMPOSITION USING A NATURAL EMULSIFYING AGENT

(71) Applicant: AMOREPACIFIC CORPORATION, Seoul (KR)

(72) Inventors: Byung Ryol Paik, Yongin-si (KR); Hui Kyoung Chang, Yongin-si (KR); Myeong Ryeol Lee, Yongin-si (KR); Yong Joo Na, Yongin-si (KR); Lee Kyoung Kwon, Yongin-si (KR); Young So Kim, Yongin-si (KR); Sang Hoon Han, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 0 days.

(21) Appl. No.: 15/712,363

(22) Filed: Sep. 22, 2017

(65) Prior Publication Data

US 2018/0008521 A1 Jan. 11, 2018

Related U.S. Application Data

(63) Continuation of application No. 14/186,225, filed on Feb. 21, 2014, now abandoned.

(51) Int. Cl.
| | | |
|---|---|---|
| *A61K 8/60* | (2006.01) | |
| *A61Q 19/02* | (2006.01) | |
| *A61K 8/06* | (2006.01) | |
| *A61Q 19/00* | (2006.01) | |
| *A61K 8/73* | (2006.01) | |

(52) U.S. Cl.
CPC ............... *A61K 8/60* (2013.01); *A61K 8/062* (2013.01); *A61K 8/604* (2013.01); *A61K 8/73* (2013.01); *A61Q 19/00* (2013.01); *A61Q 19/02* (2013.01); *A61K 2800/596* (2013.01)

(58) Field of Classification Search
CPC .... A61K 2800/596; A61K 8/062; A61K 8/60; A61K 8/604; A61K 8/73; A61Q 19/00; A61Q 19/02
See application file for complete search history.

(56) References Cited

U.S. PATENT DOCUMENTS

| | | |
|---|---|---|
| 6,218,345 B1 | 4/2001 | Brooks et al. |
| 7,157,413 B2 | 1/2007 | Lazzeri et al. |
| 8,283,304 B2 | 10/2012 | Saint Victor |
| 8,636,982 B2 | 1/2014 | Tamarkin et al. |
| 2002/0045554 A1 | 4/2002 | Hayward et al. |
| 2004/0151793 A1 | 8/2004 | Paspaleeva-kuhn et al. |
| 2006/0110415 A1 | 5/2006 | Gupta |
| 2008/0220031 A1 | 9/2008 | Wunsch et al. |
| 2010/0247458 A1 | 9/2010 | Kakoki et al. |
| 2010/0247689 A1 | 9/2010 | Paspaleeva-Kuhn et al. |
| 2012/0021960 A1 | 1/2012 | Wenk et al. |

FOREIGN PATENT DOCUMENTS

| | | |
|---|---|---|
| KR | 10-2010-0059279 | 6/2010 |
| WO | WO 2006/121610 | 11/2006 |

OTHER PUBLICATIONS

Agubata et al.; Effect of Oil, Surfactant and Co-Surfactant Concentrations on the Phase Behavior, Physicochemical Properties and Drug Release from Self-Emulsifying Drug Delivery Systems. Drug Discov Develop and Deliv. 2014; 1 (1 ):1-7.
Gullapalli et al.; Influence of an optimized non-ionic emulsifier blend on properties of oil-in-water emulsions. European Journal of Pharmaceutics and Biopharmaceutics 48 (1999):233-238.
Howe et al.; Rheology and stability of oil-in-water nanoemulsions stabilised by anionic surfactant and gelatin 2) addition of homologous series of sugar-based co-surfactants. Advances in Colloid and Interface Science 144 (2008) 30-37.
Li et al.; Molecular behavior and synergistic effects between sodium dodecylbenzene sulfonate and Triton X-100 at oil/water interface. Journal of Colloid and Interface Science 307 (2007) 215-220.
Narayanan.; Interfacial Processes and Molecular Aggregation of Surfactants, p. 85, 2008.
Peng et al.; Optimization of water-in-oil nanoemulsions by mixed surfactants. Colloids and Surfaces A: Physicochem. Eng. Aspects 370 (2010) 136-142.

*Primary Examiner* — Robert A Wax
*Assistant Examiner* — Olga V. Tcherkasskaya
(74) *Attorney, Agent, or Firm* — Nixon & Vanderhye P.C.

(57) ABSTRACT

The present invention relates to a low-viscosity cosmetic composition and methods using a natural emulsifying agent. More specifically, the present invention relates to a cosmetic composition using a naturally derived saccharide-based surfactant in place of a chemical surfactant and realizing a low-viscosity formulation to offer safety to the skin, feel good on the skin with fast absorption, give stability to the formulation and add luster to the skin in an effective manner.

4 Claims, No Drawings

LOW VISCOUS COSMETIC COMPOSITION USING A NATURAL EMULSIFYING AGENT

This application is a continuation of U.S. application Ser. No. 14/186,225 filed Feb. 21, 2014, the entire contents of which are hereby incorporated by reference.

BACKGROUND OF THE INVENTION

Field of the Invention

The present invention relates to a low-viscosity cosmetic composition using a natural emulsifying agent and, more particularly to an oil-in-water type cosmetic composition that realizes a low-viscosity formulation using a naturally derived saccharide-based surfactant in place of a synthetic surfactant to offer safety to the skin, feel good on the skin with fast absorption, give stability to the formulation and add luster to the skin in an effective manner.

Background Art

There are emulsion type cosmetics of various kinds, such as creams, lotions, etc., available to protect the skin and keep it in healthy condition. Such emulsion type cosmetics are required to exert the sufficient effects of oil-soluble ingredients, feel good on the skin and secure stability of preservation while being used after opening.

With an increase in the attention to the skin safety in recent years, many customers prefer cosmetics made of natural ingredients. But, natural surfactants are likely to be inferior in the emulsifying capacity to synthetic surfactants. On the other hand, low-viscosity oil-in-water type formulations is quite a thin consistency to feel good on the skin with fast absorption and advantageously enhances the luster of the skin in contrast to the solubilized low-viscosity formulations. However, low-viscosity formulations have difficulty in achieving stability. Low-viscosity formulations are more difficult to make with a naturally derived surfactant which has a low emulsifying capacity. It is therefore one problem in the field of cosmetics to prepare a stable low-viscosity oil-in-water type cosmetic composition using a naturally derived surfactant.

One method to prepare a stable low-viscosity oil-in-water type cosmetic composition is preparing a nano-emulsion. Typically, by preparing a nano-emulsion, the particle size is minimized to allow the composition in Brownian motion not affected by the gravity, thereby securing the stability of the formulation. The representative method of preparing a nano-emulsion is the high pressure emulsification method. But, the high pressure emulsification method uses a strong physical force in preparing a nano-emulsion and thus requires the use of a microfluidizer, causing additional energy consumption. With a succession of publications of studies on the toxic properties of nano-cosmetics, the high pressure emulsification method is not suitable as a method for preparing a cosmetic composition for improving skin stability in the aspect of the safety to the human body.

The selection of surfactants to secure long-term stability to the maximum is a problem to solve in order to prepare a stable oil-in-water type cosmetic composition with a combination of naturally derived surfactants having a low emulsifying capacity. Such an appropriate combination of natural surfactants is very difficult to find. Further, the proper content range of the oil-soluble ingredient used in combination with the natural surfactants is also of great importance.

DISCLOSURE OF INVENTION

Technical Problem

In an attempt to search for a combination of naturally derived surfactants suitable for implementation of a low-viscosity oil-in-water type cosmetic composition, the inventors of the present invention have revealed the interactions between naturally derived surfactants and natural oil-soluble ingredients and found out that the interactions can be used to lower the viscosity of the cosmetic composition, maintain the stability to the maximum and improve the skin safety.

It is therefore an object of the present invention to provide a cosmetic composition using a naturally derived surfactant to provide a low-viscosity oil-in-water type formulation with skin safety and fast absorption into the skin and thus enhance the luster of the skin.

Technical Solution

To achieve the object of the present invention, there is provided a cosmetic composition that includes a mixture of a saccharide-based surfactant having a relatively large hydrophilic portion and a saccharide-based surfactant having a relatively small hydrophilic portion; and a natural oil-soluble ingredient.

Advantageous Effects

The cosmetic composition of the present invention uses a naturally derived surfactant and a natural oil-soluble ingredient, so it is non-irritating, of low-viscosity, stable in formulation, with a light feeling, easily absorbed into the skin and more effective in enhancing the luster of the skin. Also, the cosmetic composition of the present invention uses a whitening component as well to provide more effective whitening and lustering effects for the skin.

BEST MODE FOR CARRYING OUT THE INVENTION

The present invention provides a low-viscosity cosmetic composition containing a naturally derived surfactant and a natural oil-soluble ingredient, and more particularly an oil-in-water type cosmetic composition.

The cosmetic composition of the present invention is a low-viscosity oil-in-water type emulsion using a naturally derived saccharide-based surfactant instead of a synthetic surfactant and a natural oil-soluble ingredient to offer a great skin safety and secure improved formulation stability. Also, the cosmetic composition can enhance the luster of the skin and provide a great whitening effect.

The oil-in-water type cosmetic composition of the present invention has a low viscosity of 1,000 to 4,000 cps. The viscosity of the cosmetic composition less than 1,000 cps provides poor stability, while the viscosity of the cosmetic composition greater than 4,000 cps undesirably leads to difficulty of securing a thin constancy of the cosmetic composition.

In order to use a naturally derived surfactant with enhanced emulsifying capacity, the present invention employs a mixture of a natural saccharide-based surfactant having a relatively large hydrophilic portion and a natural saccharide-based surfactant having a relatively small hydrophilic portion. A combination of the saccharide-based surfactant having a relatively large hydrophilic portion and the saccharide-based surfactant having a relatively small hydrophilic portion at a predetermined ratio can make oil particles packed with the interfacial membrane in an effective manner to stabilize the oil-in-water formulation. In this regard, the formulation stability can be achieved because the saccharide-based surfactant having a relatively small hydrophilic portion compactly fills in the gap between the interfacial membranes consisting of the saccharide-based surfactant having a relatively high hydrophilic portion.

In the present invention, among the naturally derived saccharide-based surfactants, the surfactant having a relatively small hydrophilic portion may include at least one selected from the group consisting of sucrose fatty acid ester, cetearyl glucoside, arachidyl glucoside, C12-20 alkylglucoside, etc., of which the hydrophilic portion consists of a monosaccharide or a disaccharide such as sucrose, glucoside of the like and thus has a relatively small volume. Further, the surfactant having a relatively large hydrophilic portion may include at least one selected from the group consisting of polyglyceryl-3 methylglucose distearate, inulin lauryl carbamate, etc., of which the hydrophilic portion consists of a polymer of monosaccharide or polysaccharide such as inulin or the like and thus has a relatively large volume. Most preferably, the surfactant may be a mixture of C12-20 alkylglucoside and inulin lauryl carbamate.

The cosmetic composition of the present invention contains the mixture of naturally derived saccharide-based surfactants at an amount of 0.20 wt. % to 1.50 wt. % with respect to the total weight of the composition. The content of the mixture of naturally derived saccharide-based surfactants less than 0.20 wt. % leads to low emulsion stability to induce the phase separation, while the content of the mixture of naturally derived saccharide-based surfactants greater than 1.50 wt. % undesirably causes the viscosity of the composition greater than 4,000 cps. Supposing that the content of the natural saccharide-based surfactant having a relatively large hydrophilic portion is 1, the weight ratio of the natural saccharide-based surfactant having a relatively small hydrophilic portion to the natural saccharide-based surfactant having a relatively large hydrophilic portion is preferably in the range of 0.4 to 2.5. If the mixing ratio is out of the above-defined range, the emulsion stability can be so low to cause the phase separation.

The naturally derived oil-soluble ingredient as used in the present invention may include at least one selected from solid ingredients, including a surfactant having a melting temperature of 30° C. or above and being in the solid state at the room temperature, fat, wax, higher alcohol, higher fatty acid, and hydrocarbon; or liquid ingredients, including oil, ester, hydrocarbon.

More specifically, the solid ingredients may include, for example, surfactants, such as sucrose fatty acid ester, cetearyl glucoside, inulin lauryl carbamate, C12-20 alkylglucoside, ammonium lauryl sulfate, sodium lauryl glucose carboxylate, lauryl glucoside, hydrogenated lecithin, lecithin, caprylyl/capryl glucoside, etc.; fats, such as Shea butter, mango seed butter, cacao seed butter, etc.; waxes, such as myristyl myristate, *Camellia sinensis* leaf extract, jojoba, sunflower seed, carnauba wax, candelilla wax, bee wax, etc.; higher alcohols, such as cetyl alcohol, stearyl alcohol, behenyl alcohol, etc.; higher fatty acids, such as caprylic/capric triglyceride, lauric acid, myristic acid, palmitic acid, stearic acid, etc.; and hydrocarbons, such as ceresin, etc. The liquid ingredients may include, for example, oils, such as meadowfoam seed oil, sunflower seed oil, macadamia seed oil, green tea seed oil, coconut oil, olive oil, camellia oil, etc.; esters, such as phytosteryl/octyldodecyl lauroyl glutamate, isostearyl isostearate, methylheptyl isostearate, dicaprylyl carbonate, isopropyl palmitate, etc.; ethers, such as dicaprylyl ether, etc.; and hydrocarbons, such as squalane, etc.

The cosmetic composition of the present invention contains the oil-soluble ingredient in an amount of 5 wt. % to 15 wt. % with respect to the total weight of the composition. The term "the content of the oil-soluble ingredient" as used herein means the total weight of the oil-soluble component excluding the surfactant which is an emulsifying agent. The content of the oil-soluble ingredient less than 5 wt. % leads to failure to provide the effect as an emulsion type cosmetic, while the content of the oil-soluble ingredient greater than 15 wt. % undesirably ends up having difficulty of securing the formulation stability.

The present invention may further use an additional whitening ingredient in order to enhance the effect of lustering the skin and provide a whitening effect. In the present invention, the whitening ingredient may further include at least one selected from the group consisting of, particularly, green tea polysaccharide, mushroom-derived yeast extract, and niacinamide. These whitening ingredients are effective to reduce melanin pigments and create a synergy in regards to the whitening efficacy, improving the whitening effect.

Among the whitening ingredients used in the present invention, the green tea polysaccharide which is isolated from green tea powder through hot-water extraction, ultrafiltration, and ethanol precipitation inhibits the production of melanin and the expression of MMP-1 (Matrix metalloproteinase-1) and increases the moisturizing ability of the skin to provide a good whitening effect. Also, the mushroom-derived yeast extract which is separated from truffles by enzyme hydrolysis and heat treatment intensifies the activities of LC3 (Light chain 3) protein and lysosome participating in the autophagy process in the epidermal keratinocytes to eliminate waste matters from the skin, thus making the skin light and clear. Finally, niacinamide which is a vitamin B3 component inhibits the transfer of melanin from the cells that produce melanin to the surface of the skin to help reduce pigmentation and improve the skin tone. In particular, these ingredients, such as green tea polysaccharide, mushroom-derived yeast extract, and niacinamide, as used in the present invention function on the respective steps of the skin whitening process to provide a synergy, so they are all desirably used in combination.

Among the skin whitening ingredients, the cosmetic composition of the present invention may contain green tea polysaccharide and mushroom-derived yeast extract in an amount of 0.01 wt. % to 5.0 wt. % with respect to the total weight of the composition. The content of green tea polysaccharide and mushroom-derived yeast extract less than 0.01 wt. % is too insignificant to provide the skin whitening effect, while the content of green tea polysaccharide and mushroom-derived yeast extract greater than 5.0 wt. % undesirably causes skin irritation. On the other hand, the content of niacinamide may be 2 wt. %, which is usually accepted as the effective amount.

The cosmetic composition of the present invention may further contain an appropriate amount of auxiliary ingredients typically used in the preparation of oil-in-water type cosmetics, such as colors, fragrances, preservatives, thickening agents, and so forth. Preferably, the content of the auxiliary ingredients may be 0 to 20 wt. % with respect to the total weight of the cosmetic composition.

In consideration of the low-viscosity characteristic, if not specifically limited in the formulation, the cosmetic composition of the present invention may be formulated into a wide variety of applications, including fundamental skin cosmetic compositions, such as skin toner, nutrient toner, gel, lotion, etc.; hair-care cosmetic compositions, such as hair tonic, hair essence, hair restorer such as hair treatment, etc.; and other drugs and quasi-drugs.

Hereinafter, the present invention will be described in further detail with reference to the examples and experimental examples, which are given only for better understanding of the present invention. So it should be understood that modifications, substitutions, or additions as known in the related art could be made thereto without departing from the spirit and scope of the invention.

[Reference Example] Preparation of Examples and Comparative Examples

The oil-in-water type emulsions of Examples 1 to 5 and Comparative Examples 1 to 6 are prepared in the manner as described in the following preparation method according to the composition as given in Tables 1 and 2.

TABLE 1

| | | Example | | | | |
|---|---|---|---|---|---|---|
| No | Ingredient | 1 | 2 | 3 | 4 | 5 |
| 1 | C14-22 alcohol * C12-20 alkylglucoside | 0.50 | 0.50 | 0.50 | 0.50 | 0.50 |
| 2 | Vegetable squalane | 3.00 | 3.00 | 3.00 | 3.00 | 3.00 |
| 3 | Dicaprylyl carbonate | 4.00 | 4.00 | 4.00 | 4.00 | 4.00 |
| 4 | Dicaprylyl ether | 2.00 | 2.00 | 2.00 | 2.00 | 2.00 |
| 5 | Caprylic/capric triglyceride | 2.00 | 2.00 | 2.00 | 2.00 | 2.00 |
| 6 | Cetearyl alcohol * glyceryl stearate * stearic acid * hydrogenated lecithin* polyglyceryl-3-methyl glucose distearate | 0.50 | 0.50 | 0.50 | 0.50 | 0.50 |
| 7 | Butyrospermum parkii (shea butter) extract (shea butter (organic)) | 0.50 | 0.50 | 0.50 | 0.50 | 0.50 |
| 8 | Stearyl glycyrrhetinate | 0.01 | 0.01 | 0.01 | 0.01 | 0.01 |
| 9 | Purified water | To 100 | To 100 | To 100 | To 100 | To 100 |
| 10 | Disodium EDTA | 0.02 | 0.02 | 0.02 | 0.02 | 0.02 |
| 11 | Niacinamide, nicotiamide (BP) | 0.00 | 2.00 | 2.00 | 2.00 | 2.00 |
| 12 | Inulin lauryl carbamate | 0.40 | 0.40 | 0.40 | 0.40 | 0.40 |
| 13 | Xanthan gum | 0.15 | 0.15 | 0.15 | 0.15 | 0.15 |
| 14 | Dipropylene glycol | 2.00 | 2.00 | 2.00 | 2.00 | 2.00 |
| 15 | Tromethamine | 0.05 | 0.05 | 0.05 | 0.05 | 0.05 |
| 16 | Phenoxyethanol | 0.30 | 0.30 | 0.30 | 0.30 | 0.30 |
| 17 | Ethylhexyl glycerin | 0.05 | 0.05 | 0.05 | 0.05 | 0.05 |
| 18 | Butylene glycol | 5.00 | 5.00 | 5.00 | 5.00 | 5.00 |
| 19 | Hydroxyethyl acrylate/sodium acryloyl dimethyl taurate copolymer | 0.30 | 0.30 | 0.30 | 0.30 | 0.30 |
| 20 | Purified water | 8.00 | 8.00 | 8.00 | 8.00 | 8.00 |
| 21 | Carbomer | 0.08 | 0.08 | 0.08 | 0.08 | 0.08 |
| 22 | Broussonetia kazinoki root extract * propanediol * ginko biloba leaf extract * butylene glycol * glycyrrhiza glabra (licorice) root extract | 1.00 | 1.00 | 1.00 | 1.00 | 1.00 |
| 23 | Purified water * butylene glycol * camellia sinensis leaf extract * caprylyl glycol * 1,2-hexanediol | 0.00 | 0.00 | 1.00 | 0.00 | 0.50 |
| 24 | Butylene glycol * silybum marianum fruit extract | 0.10 | 0.10 | 0.10 | 0.10 | 0.10 |

TABLE 1-continued

| | | Example | | | | |
|---|---|---|---|---|---|---|
| No | Ingredient | 1 | 2 | 3 | 4 | 5 |
| 25 | Mushroom-derived yeast extract | 0.00 | 0.00 | 0.00 | 1.00 | 0.50 |
| 26 | Butylene glycol | 3.00 | 3.00 | 3.00 | 3.00 | 3.00 |
| 27 | Resveratrol (10%) (methylmethacrylate/ acrylonitrile copolymer/resveratrol) | 0.01 | 0.01 | 0.01 | 0.01 | 0.01 |
| 28 | Compound fragrance | 0.15 | 0.15 | 0.15 | 0.15 | 0.15 |

TABLE 2

| | | Comparative Example | | | | | |
|---|---|---|---|---|---|---|---|
| No | Ingredient | 1 | 2 | 3 | 4 | 5 | 6 |
| 1 | C14-22 alcohol * C12-20 alkyl glycoside | 0.10 | 0.50 | 0.15 | 1.15 | 0.50 | 0.50 |
| 2 | Vegetable squalane | 3.00 | 3.00 | 3.00 | 3.00 | 1.00 | 4.00 |
| 3 | Dicapryryl carbonate | 4.00 | 4.00 | 4.00 | 4.00 | 1.00 | 5.00 |
| 4 | Dicaprylyl ether | 2.00 | 2.00 | 2.00 | 2.00 | 1.00 | 3.00 |
| 5 | Caprylic/capric triglyceride | 2.00 | 2.00 | 2.00 | 2.00 | 0.50 | 3.00 |
| 6 | Cetearyl alcohol * glyceryl stearate * stearic acid * hydrogenated lecithin* polyglyceryl-3-methyl glucose distearate | 0.50 | 0.50 | 0.50 | 0.50 | 0.50 | 1.00 |
| 7 | Butyrospermum parkii (shea butter) extract (shea butter (organic)) | 0.50 | 0.50 | 0.50 | 0.50 | 0.50 | 1.00 |
| 8 | Stearyl glycyrrhetinate | 0.01 | 0.01 | 0.01 | 0.01 | 0.01 | 0.01 |
| 9 | Purified water | To 100 | To 100 | To 100 | To 100 | To 100 | To 100 |
| 10 | Disodium EDTA | 0.02 | 0.02 | 0.02 | 0.02 | 0.02 | 0.02 |
| 11 | Niacinamide, nicotiamide (BP) | 0.00 | 0.00 | 0.00 | 0.00 | 0.00 | 0.00 |
| 12 | Inulin lauryl carbamate | 0.08 | 0.00 | 0.40 | 0.40 | 0.40 | 0.40 |
| 13 | Xanthan gum | 0.15 | 0.15 | 0.15 | 0.15 | 0.15 | 0.15 |
| 14 | Dipropylene glycol | 2.00 | 2.00 | 2.00 | 2.00 | 2.00 | 2.00 |
| 15 | Tromethamine | 0.05 | 0.05 | 0.05 | 0.05 | 0.05 | 0.05 |
| 16 | Phenoxyethanol | 0.30 | 0.30 | 0.30 | 0.30 | 0.30 | 0.30 |
| 17 | Ethylhexyl glycerin | 0.05 | 0.05 | 0.05 | 0.05 | 0.05 | 0.05 |
| 18 | Butylene glycol | 5.00 | 5.00 | 5.00 | 5.00 | 5.00 | 5.00 |
| 19 | Hydroxyethyl acrylate/sodium acryloyl dimethyl taurate copolymer | 0.30 | 0.30 | 0.30 | 0.30 | 0.30 | 0.30 |
| 20 | Purified water | 8.00 | 8.00 | 8.00 | 8.00 | 8.00 | 8.00 |
| 21 | Carbomer | 0.08 | 0.08 | 0.08 | 0.08 | 0.08 | 0.08 |
| 22 | Broussonetia kazinoki root extract * propanediol * ginko biloba leaf extract * butylene glycol * glycyrrhiza glabra (licorice) root extract | 1.00 | 1.00 | 1.00 | 1.00 | 1.00 | 1.00 |
| 23 | Purified water * butylene glycol * camellia sinensis leaf extract * caprylyl glycol * 1,2-hexanediol | 0.00 | 0.00 | 0.00 | 0.00 | 0.00 | 0.00 |
| 24 | Butylene glycol * silybum marianum fruit extract | 0.10 | 0.10 | 0.10 | 0.10 | 0.10 | 0.10 |
| 25 | Mushroom-derived yeast extract | 0.00 | 0.00 | 0.00 | 0.00 | 0.00 | 0.00 |
| 26 | Butylene glycol | 3.00 | 3.00 | 3.00 | 3.00 | 3.00 | 3.00 |

TABLE 2-continued

| | | Comparative Example | | | | | |
|---|---|---|---|---|---|---|---|
| No | Ingredient | 1 | 2 | 3 | 4 | 5 | 6 |
| 27 | Resveratrol (10%) (methylmethacrylate/ acrylonitrile copolymer/resveratrol) | 0.01 | 0.01 | 0.01 | 0.01 | 0.01 | 0.01 |
| 28 | Compound fragrance | 0.15 | 0.15 | 0.15 | 0.15 | 0.15 | 0.15 |

<Preparation Method>

(1) The ingredients 9 to 17 of Table 1 are mixed together and dissolved at 70° C. to prepare a water phase.

(2) In a separate container, the ingredients 1 to 8 of Table 1 are dissolved at 70° C. to prepare an oil phase.

(3) The oil phase of the step (2) is added to the water phase of the step (1), and the mixture is blended with a homo-mixer under agitation.

(4) The ingredients 18 and 19 and the ingredients 20 and 21 are added to the mixture of the step (3), and the resultant mixture is stirred with a homo-mixture and then cooled down to 50° C.

(5) The ingredients 22 to 28 are added to the mixture of the step (4), and the resultant mixture is stirred with a homo-mixer and, after degasification, cooled down to 30° C. to prepare a cosmetic composition.

Experimental Example 1

Change of viscosity and stability on the function of the combination and content of naturally derived saccharide-based surfactants and the content of oil-soluble ingredient Each oil-in-water type emulsion of Example 1 and Comparative Examples 1 to 6 was evaluated in regards to the change of viscosity and stability on the function of the change in the combination and content of surfactants (Comparative Examples 1 to 4) and the change in the content of the oil-soluble ingredient (Comparative Examples 5 and 6). In this regard, the viscosity was measured with Spindle No. 3 at 12 rpm using a Brookfield viscometer LVDV-II (manufactured by Brookfield engineering laboratories). The measurement results are presented in Table 3.

TABLE 3

| Test substance | Viscosity (cps) | Stability | In-use feel |
|---|---|---|---|
| Example 1 | 1,630 | Good | Quite a thin constancy |
| Comparative Example 1 | 240 | Separation at 60° C. next day | Feels light |
| Comparative Example 2 | 870 | Separation at 60° C. in 7 days | Feels light |
| Comparative Example 3 | 865 | Separation at 60° C. next day | Feels light |
| Comparative Example 4 | 2,350 | Good | Feels heavy and leaves residue |
| Comparative Example 5 | 1,100 | Good | Lacks in softness |
| Comparative Example 6 | 2,120 | Separation at 30° C. immediately after preparation | Too oily |

Good: Typically, considered to secure 4-week stability in a cycle pyrostat at −10° C., 5° C., 30° C., 37° C., 45° C. or 60° C.

As can be seen from the results of Table 3, the oil-in-water type emulsion of Example 1 having the combination and content of naturally derived saccharide-based surfactants and the content of the oil-soluble ingredient according to the present invention can secure formulation stability and light feel with a thin constancy at the target viscosity of 4,000 cps or below. Contrarily, the oil-in-water type emulsion which contains the naturally derived saccharide-based surfactants at an amount of less than 0.20 wt. % (Comparative Example 1) has an extremely low viscosity and undergoes phase separation at high temperature the next day without securing formulation stability. The oil-in-water type emulsion which contains the naturally derived saccharide-based surfactants at an amount of greater than 1.50 wt. % (Comparative Example 4) secures formulation stability but has an extremely high viscosity to offer a thin consistency, leaving residues on the skin. Further, the oil-in-water type emulsion undergoes phase separation at high temperature and fails to secure formulation stability when it does not contain either one of the saccharide-based surfactant having a relatively large hydrophilic portion or the saccharide-based surfactant having a relatively small hydrophilic portion or has an inappropriate combination of the saccharide-based surfactant having a relatively large hydrophilic portion and the saccharide-based surfactant having a relatively small hydrophilic portion (Comparative Examples 2 and 3). Finally, the oil-in-water type emulsion which contains the oil-soluble ingredient at an amount of less than 5 wt. % (Comparative Example 5) lacks in softness, and the oil-in-water type emulsion which contains the oil-soluble ingredient at an amount of greater than 15 wt. % (Comparative Example 6) fails to emulsify and undergoes phase separation at the room temperature.

[Experimental Example 2] Measurement of Skin Melanin Index According to the Content of Whitening Ingredient To evaluate the whitening effect of the cosmetic compositions of Examples 1 to 5, thirty-one healthy women who are 25 to 35 years old with at least third-degree hyperpigmentation on the face according to SOP are told to use each emulsion for 8 weeks to measure the skin lightness and the melanin index after the applications. More specifically, thirty-one women are divided into two groups: the one consists of 15 women, the other 16 women. Each group uses two compositions. The melanin index is measured with a Mexameter three times on the hyperpigmented region and the non-pigmented region before the application of each emulsion and after 8 weeks of application. The melanin index is used to calculate the improvement rate of melanin index according to the following equation 1 and then averaged. The results are presented in Table 4.

$$\text{Improvement rate (\%) of melanin index} = \frac{\text{Melanin index after 8 weeks} - \text{Melanin index before use}}{\text{Melanin index before use}} \times 100 \quad \text{[Equation 1]}$$

TABLE 4

| | | Measurement results Example | | | | |
|---|---|---|---|---|---|---|
| Index | Measured region | 1 | 2 | 3 | 4 | 5 |
| Improvement rate (%) of | Hyperpigmented region | −0.07 | −3.21 | −4.68 | −4.13 | −7.34 |

TABLE 4-continued

| Index | Measured region | Measurement results Example | | | | |
|---|---|---|---|---|---|---|
| | | 1 | 2 | 3 | 4 | 5 |
| melanin index | Non-pigmented region | −0.03 | −3.01 | −3.45 | −3.14 | −5.84 |

As can be seen from Table 4, the cosmetic composition containing none of green tea polysaccharide, mushroom-derived yeast extract and niacinamide (Example 1) shows the melanin index improving effect after 8 weeks. The cosmetic composition containing niacinamide (Example 2) has the melanin index improving effect. The cosmetic composition containing either a combination of niacinamide and green tea polysaccharide or a combination of niacinamide and mushroom-derived yeast extract (Example 3 or 4) exerts the greater effect to improve the melanin index. Also, the cosmetic composition containing all the three ingredients of niacinamide, green tea polysaccharide and mushroom-derived yeast extract (Example 5) provides the synergy effect to remarkably reduce the melanin index.

What is claimed is:

1. A method for enhancing luster of skin and whitening skin of a subject, comprising applying to the skin of the subject a cosmetic composition containing:
   a mixture of a first naturally-derived saccharide-based surfactant selected from the group consisting of polyglyceryl-3-methyl glucose distearate, inulin lauryl carbamate, and a mixture thereof; and a second naturally-derived saccharide-based surfactant selected from the group consisting of sucrose fatty acid ester, cetearyl glucoside, arachidyl glucoside, C12-20 alkylglucoside, and a mixture thereof;
   a naturally-derived oil-soluble ingredient; and
   a mixture of niacinamide and at least one ingredient selected from the group consisting of green tea polysaccharide and mushroom-derived yeast extract; and
   wherein a weight ratio of the first naturally-derived saccharide-based surfactant to the second naturally-derived saccharide-based surfactant is 0.4 to 2.5;
   wherein the composition has a viscosity of 1,000 cps to 4,000 cps as measured with Spindle No. 3 at 12 rpm using a Brookfield viscometer;
   wherein the composition contains a mixture of the first naturally-derived saccharide-based surfactant and the second naturally-derived saccharide-based surfactant in an amount of 0.20 wt. % to 1.50 wt. % with respect to the total weight of the composition;
   wherein the composition contains the naturally-derived oil-soluble ingredient in an amount of 5 wt. % to 15 wt. % with respect to the total weight of the composition;
   wherein the content of the at least one ingredient selected from green tea polysaccharide and mushroom-derived yeast extract is 0.01 wt. % to 5.0 wt. % with respect to the total weight of the composition; and
   wherein the content of the niacinamide is 2 wt. % with respect to the total weight of the composition.

2. The method as claimed in claim 1, wherein the composition is an oil-in-water composition.

3. The method as claimed in claim 1, wherein the naturally-derived oil-soluble ingredient comprises: a solid oil-soluble ingredient having a melting temperature of 30° C. or above and being in a solid state at room temperature; or a liquid oil-soluble ingredient comprising at least one ingredient selected from the group consisting of an oil, an ester, and a hydrocarbon, and wherein the liquid oil-soluble ingredient is in the liquid state at room temperature.

4. The method as claimed in claim 1, wherein the composition comprises all of the green tea polysaccharide, mushroom-derived yeast extract and niacinamide.

* * * * *